US006495170B1

(12) United States Patent
Smit et al.

(10) Patent No.: US 6,495,170 B1
(45) Date of Patent: Dec. 17, 2002

(54) METHOD OF INCREASING THE PRESENCE OF GLUTATHIONE IN CELLS

(75) Inventors: Hobbe Friso Smit, Utrecht (NL); Klaske van Norren, Renkum (NL); Robert Johan Joseph Hageman, Waddinxveen (NL)

(73) Assignee: N. V. Nutricia, Zoetermeer (NL)

( * ) Notice: Subject to any disclaimer, the term of this patent is extended or adjusted under 35 U.S.C. 154(b) by 0 days.

(21) Appl. No.: 09/639,469

(22) Filed: Aug. 16, 2000

(51) Int. Cl.[7] .......................... A61K 35/78; A61K 31/70
(52) U.S. Cl. ..................... 424/725; 424/70.51; 514/22; 514/23; 514/783; 514/893
(58) Field of Search ............................. 424/725, 70.51; 435/113; 514/25, 26, 24, 42, 4.1, 893, 22, 2, 12

(56) References Cited

U.S. PATENT DOCUMENTS

| 5,747,459 A | * | 5/1998 | Rowe et al. |
| 5,929,038 A | * | 7/1999 | Chang |
| 6,013,663 A | * | 1/2000 | Fujita et al. |
| 6,030,950 A | * | 2/2000 | Ohlenschlager |
| 6,132,727 A | * | 10/2000 | Rohde, Jr. et al. |
| 6,197,295 B1 | * | 3/2001 | Hsia et al. |
| 6,262,019 B1 | * | 7/2001 | Keller et al. |

FOREIGN PATENT DOCUMENTS

| DE | 2203884 | * | 8/1973 |
| DE | 3628010 | * | 2/1988 |
| EP | 0276317 | * | 7/1987 |
| JP | 360258115 | * | 12/1985 |
| JP | 2000302784 | * | 10/2000 |
| WO | WO 99/433366 | * | 9/1999 |

OTHER PUBLICATIONS

Lapperre et al., FEBS Letters (1999); 443: 235–239. Apocynin increases glutathione synthesis and activates AP=1 in alveolar epithelial cells.*
Ip et al., Biochem Pharm (1997); 54: 317–319. Methlenedioxy group as determinant of schisandrin in enhancing hepatic mitochondrial glutathione in carbon tetrachloride–intoxicated mice.*
Rastogi et al., Drug Devel Res (1997); 41: 44–47. Effect of Picroliv on impaired hepatic mixed–function oxidase system in carbon tetrachloride–intoxicated mice.*
Rastogi et al., Phytother Res (1995); 9: 364–367. Efffect of Picrolic on antioxidant–system in liver of rats, after partial hepatectomy.*
Wang et al., Yunnan Zhiwu Yanju (1993); 15(1): 83–8. Chemical constituents of Picrorhiza scrophulariiflora.*
Brochure of a Hepafyt composition, May 1999.

* cited by examiner

Primary Examiner—Christopher R. Tate
Assistant Examiner—Michele C. Flood
(74) Attorney, Agent, or Firm—Bacon & Thomas

(57) ABSTRACT

A method for increasing the presence of glutathione in cells including treating or preventing impaired liver function by administering a composition which includes a precursor of gluthathione, and enhancer of glutathione biosynthesis, and a third component which is a lignan or the third component is a combination of an enhancer of gluthathione regeneration and an enhancer of glutathione-mediated conjugation. The precursor of gluthathione is cysteine or is a functional equivalent of cysteine which yields cysteine when administered to a mammal undergoing treatment.

12 Claims, No Drawings

METHOD OF INCREASING THE PRESENCE OF GLUTATHIONE IN CELLS

DESCRIPTION

FIELD OF THE INVENTION

This invention relates to a method of increasing the presence of glutathione in cells including treating or preventing of impaired liver function by administering to a mammal in the need thereof a dietetic or pharmaceutical composition and to a corresponding dietetic or pharmaceutical composition.

BACKGROUND OF THE INVENTION

The liver is the major organ involved in metabolism of protein, carbohydrates, and fats, but is also the major organ for detoxification. Potential toxic compounds are converted into inactive metabolites by phase I-metabolising enzymes and excreted. Alternatively, metabolites are further conjugated by phase II-metabolising enzymes and excreted after all.

Many drugs and toxins can be detoxified by conjugation with glutathione. When the levels of these drugs or toxins, however, exceed the liver concentration of reduced glutathione; such components become acutely hepatotoxic. Striking is that in several kinds of liver disorders, glutathione levels are decreased, for example: in hepatitis infection, where the grade of activity of the liver disease is correlated with reduction of GSH in acute liver toxification, e.g. acetaminophen intoxication, and in alcoholics with liver failure.

Both hepatitis C and the exposure to liver toxins can lead to hepatocarcinoma, possibly via the same mechanism of incompetence of the liver to respond to toxins, either endotoxins or exo-toxins.

Reduced glutathione (GSH) is the substrate of glutathione peroxidase (GPX) and as such contributes to the antioxidant defence mechanism as well.

Glutathione reductase enzymes reduce GSSG back to GSH, predominantly in the presence of NADPH, which is provided by e.g. the oxidative pentose phosphate pathway. The capacity of the glutathione system to cope with $H_2O_2$ in liver depends on the activity of GPX and giutathione reductase, the rate of NADPH supply, and the GSH content. Except for its effects on hydrogen peroxide, GSH can also react with e.g. $OH^\circ$, HOCl, peroxynitrite, $RO^\circ$, and $RO_2^\circ$ in vitro. Upon reacting with free radicals, thiyl radicals (Gaf) are produced, which generate superoxide. Moreover, superoxide can also inactivate GPX in the absence of GSH. Hence, superoxide dismutase (SOD) or antioxidants can co-operate with GSH to remove free radicals in vivo.

Many xenobiotics supplied to living organisms are metabolised by conjugation with GSH. This process is catalysed by glutathione S-transferase enzymes (GST).

GSH is synthesised in two steps, catalysed by two different enzymes. During the first step, γ-glutamylcysteine synthetase (GCS) catalyses the formation of L-γ-glutamyl-L-cysteine from glutamate and cysteine. The second step incorporates glycine under influence of glutathione synthetase, yielding GSH.

One example of a drug that can deplete the concentration of reduced glutathione in the liver is the commonly used sedative acetaminophen (paracetamol). Acetaminophen has caused severe hepatic necrosis when ingested in large amounts, e.g. in suicide attempts or accidentally by children. Acetaminophen hepatotoxicity is mediated by a toxic reactive metabolite formed from the parent compound by the cytochrome P450 mixed-function oxidase system of the hepatocyte. The metabolite is then detoxified by conjugation with glutathione. If excessive amounts are formed, the glutathione reserves of the liver are depleted, and the quinonimine reacts with constituents of the liver cells, leading to necrosis. The hepatic injury may be potentiated by the use of alcohol or other drugs and also starvation and cachexia, conditions in which liver glutathione are lower, may potentiate the effect.

Milk thistle, or *Silybum marianum* (L.) Gaertn. (Compositae) is in Western countries well-known for its hepatoprotective effects. Its key components are flavanolignans, collectively known as silymarin. A composition for the protection, treatment and repair of liver tissue containing Milk thistle is for instance described in WO 99/43336.

Intraperitoneal administration of silymarin (200 mg/kg) in rats increased the total glutathione content and improved the reduced glutathione/oxidised glutathione ratio in the liver, intestine, and stomach, while levels of kidney, lung, and spleen were not affected (Valenzuela et al., Selectivity of silymarin on the increase of gutathione content in different tissues of the rat, Planta Medica 55, 420–2 (1989)). The main component of silymarin, silybin, exerted inhibitory effects on superoxide and hydrogen peroxide production in human neutrophils and increased the activity of both superoxide dismutase and glutathione peroxidase in human erythrocytes. Silymarin protects against acetaminophen-induced GSH depletion and cytotoxicity in hepatoblastoma Hep G2 cells in vitro. Silymarin and silybin protect in vivo against hepatic glutathione depletion induced by ethyl alcohol and paracetamol in rats. It was shown that silybin reduces the GSH depletion induced by acetaminophen, but does not affect GSH depletion by buthionine sulfoximide in isolated rat hepatocytes. This suggests that it enhances GSH oxidation or conjugation, without affecting glutamylcysteine synthetase or GSH synthesis (Garrido et al., *Pharmacology an Toxicology* 69, 9–12 (1991)).

Furthermore, silybin was found to be a potent, non-toxic, inhibitor of glutathione-S-transferase (Bartholomeus et al., *Xenobiotica* 24, 17–24, (1994)). This observation leads to the conclusion that, although silymarin might be effective as a hepatoprotective agent, secondary detoxification by conjugation to GSH, as is catalysed by GSH-transferase, is inhibited.

Silymarin treatment (Legalon, 420 mg, 6 months) in patients with chronic alcoholic liver disease in a double blind placebo controlled trial increased the serum level of free —SH groups and the activity of GSH peroxidase. Other clinical trials confirm the hepatoprotective effect of standardised Silybum extracts.

RO 102689 (Intr. Medicamente Biofarm) discloses the extraction of silymarin from armurariu fruit. Said extract shall be useful in the treatment of active chronic hepatitis, cirrhosis of the liver and for the protection of liver cells during administration of hepatoxic agents.

*Picrorhiza kurrooa* Royle (Scrophulariaceae) has been used in Ayurveda mainly for the treatment of liver disorders. Iridoid glucosides have been regarded as its active constituents; however, other compounds like acetophenones might also play a role.

Several iridoid glucosides have been isolated from *P. kurrooa*, most of them conjugates of catalpol with either benzoyl- or cinnamoyl-derived side chains.

Picroliv is a standardised fraction of *Picrorhiza kurrooa* containing the iridoid glycosides picroside I and kutkoside in a ratio of 1:1.5 to 1.2 (50–70%) and a mixture of cucurbitacin glycosides (4–5%) (U.S. Pat. No. 5,145,955). Picroside II has also been isolated from *Picrorhiza kurrooa* and 50 mg/kg p.o. in mice treated with CCl4 showed a hepatoprotective activity (DE-A 2203884).

Picroliv has been tested in a number of liver damage models in vitro and in vivo. These studies have demonstrated its antihepatotoxic, hepatoregenerative, choleretic, and hypolipidemic activities (reviewed by Dhawan, *Medicinal Chemistry Research* 5, 595–605, (1995)). Hepatoregenerative effects were associated with an increased recovery of the liver anti-oxidant system after partial hepatectomy or carbon tetrachloride-induced liver damage of Picroliv-treated rats. Furthermore, Picroliv significantly reversed paracetamol-induced biochemical changes in several liver cell markers after oral administration to rats (6 and 12 mg/kg) for 7 days. Injection of carbon tetrachloride in rats induced a drastic impairment of the hepatic mixed-function oxidase system, as indicated by several drug-metabolising enzymes such as glutathione-S-transferase and reduced glutathione. Administration of Picroliv (6 mg/kg) for 7 days significantly prevented liver damage (Rastogi et al., *Drug Development Research* 41, 44–47, (1997)). Picroliv, given to rats during the last 15 days (12 mg/kg/day p.o.) of a 45 days exposure to alcohol, prevented the decrease of superoxide dismutase, catalase, glutathione-S-transferase, and the level of reduced glutathione (Rastogi et al., 1196). Picroliv (6 mg/kg/day p.o.) recovered the depletion of reduced glutathione level and the inhibition of glutathione-S-transferase, glutathione reductase, and glutathione peroxidase activities in the livers of mice infected with *Plasmodium berghei*. (Furthermore, Picroliv recovered the decreased levels of cysteine, sulphydryl groups and glutathione synthesis by suppressing the enhanced activation of γ-glutamyl transpeptidase in mice infected with *Plasmodium berghei*. Pretreatment with the ethanol extract of *Picrorhiza kurrooa* (50 mg/kg/day, p.o.) prevented the decrease of glutathione peroxidase and glutathione transferase activity, and the decrease of reduced glutathione in rats with galactosamine-induced liver damage.

Apocynin, an acetophenone isolated from *P. kurrooa*, enhances intracellular GSH synthesis, mediated by the increased expression of γ-GCS mRNA and enzyme activity through activation of transcription factor AP-1 (Lapperre et al., Febs Letters 443, 235–9, (1999)).

*Schisandra chinensis* (Turcz.) Baill (Schisandraceae) is a winding herb found in the Far East. Its fruits have been used since long in traditional medicine in this part of the world, The main active ingredients are lignans, e.g. schisandrins (gomisins). These compounds were shown to be potent hepatoprotective agents (Hancke et al., *Fitoterapia* 70, 451–471, (1999)). They are able to enhance the GSH/GSSG ratio and the activity of GSH reductase, increasing the GSH status of liver cell mitochondria. Furthermore, they are able to enhance detoxification by enhancing cytochrome P450-mediated metabolism of hepatotoxins, followed by the induction of GSH-S-transferase-mediated conjugation.

Pretreatment with a lignan-enriched extract of *Schisandra chinensis* (1.6 g/kg p.o.) enhanced the hepatic glutathione status and protected against physical exercise-induced muscle damage in rats (Ko et al., Phytotherapy Research 10, 450–452, (1996)). Treatment of rats with extract from *Schisandra chinensis* (1.6 g/kg/day p.o.) increased the hepatic GSH level and activities of GSH reductase, G6PDH, and decreased the susceptibility of hepatic tissue homogenates to peroxide-induced GSH depletion; pretreating rats with these extracts (0.2–3.2 9/g/kg p.o.) dose-dependently protected against CCl4-induced GSH-depletion and oxidative hepatocellular damage. These data were confirmed by other experiments, showing that *Schisandra chienesis* extract (1.6 g/kg/day p.o.) increases hepatic GSH levels, GSH reductase and GSH-transferase activities and prevents liver damage in rats with aflatoxin- and cadmium-induced liver damage. Pretreatment of schisanhenol and schizandrin B (200 mg/kg) to mice with ethanol-induced liver peroxidation increased dismutase and catalase activity, while GSH-peroxidase activity was unaffected. Treatment of schisandrin B (3 mmol/kg/day p.o.) increased the mitochondrial GSH level and reciprocally decreased GSSG level, elevating the GSH/GSSG ratio, and increased mitochondrial GSH reductase activity. These effects were more pronounced in CCl4-intoxicated mice, providing protection against liver damage. BCNU, a specific inhibitor of GSH reductase, however, did not affect the protective activity, although it inhibited GSH reductase activity, suggesting that the enhancement of GSH reductase activity by Schisandrin B is not a primary factor of hepatoprotection.

The direct antioxidants are radical scavengers by their chemical composition or interfere with the formation of oxygen radicals. The antioxidants most commonly known for this function are vitamin C, vitamin E and flavonoids. Catechins from green tea and curcumin have similar effects and enhance the antioxidant activity.

Selenium is a component of glutathione peroxidase in erythrocytes and other tissues. Glutathione peroxidase reduces hydrogen peroxide to water. Selenium is thought to be well-absorbed both as inorganic selenium salts and organic selenium compounds. A 200 µg/day supplement for 2 months in selenium-deficient patients with alcoholic cirrhosis significantly improved plasma selenium levels and glutathione peroxidase but had no effect on peroxidative parameters.

Zinc has a role in protection against oxygen radical damage, being an essential component of cytoplasmic superoxide dismutase. Zinc ions also bind to sulphydryl groups in proteins, protecting them against oxidation. Most (80–85%) plasma zinc is bound to albumin, 15% to alpha2-macroglobulin and <2% to RBP. Plasma zinc levels are depressed by infections and other stressors, probably due to systemic redistribution mediated by metallothionein, and perhaps because plasma albumin levels are reduced in stress.

Copper is an essential part of many enzymes which are involved in protection against free radical damage, e.g. cytochrome oxidase, lysyl oxidase, Zn/Cu superoxide dismutase. About 30% of dietary copper is absorbed, and there is some evidence that this increases in deficiency. Dietary deficiency is extremely rare. Over 80% of plasma copper is bound to ceruloplasmin (a positive acute phase protein that increases in inflammatory conditions). Free copper ions (unlikely in normal conditions but may occur in the case of copper excess) are a major source of oxygen radicals.

Manganese is part of a number of metalloenzymes, including mitochondrial pyruvate carboxylase, superoxide dismutase and acetyl CoA carboxylase.

SUMMARY OF THE INVENTION

It is a primary object of the present invention to provide a method of increasing the presence of glutathione in cells including the prevention or treatment of impaired liver function by administering a certain combination of components to a mammal.

It is a further object of the present invention to provide improved compositions for increasing the presence of glutathione in cells including the prevention or treatment of impaired liver function.

It was surprisingly found that a combination of components is required for providing an optimal protection against liver damage. It was found that, for this purpose, a combination is required with components that enhance the glutathione status of the cells. In order to achieve this, components are administered which are precursors for the endogenous glutathione production. Together therewith components are administered which enhance the endogenous glutathione biosynthesis and which enhance the regeneration of oxidised glutathione and/or enhance the glutathione-mediated conjugation.

DETAILED DESCRIPTION OF THE INVENTION

The present invention provides a method of increasing the presence of glutathione in cells including the prevention or treatment of impaired liver function and novel dietetic or pharmaceutical compositions for said purpose comprising in combination at least a) one precursor of glutathione which is selected from the group consisting of cysteine and functional equivalents containing said amino acid, b) one enhancer of the glutathione biosynthesis, and c) a third component which is either selected from lignans or which is a combination c1) of an enhancer of glutathione regeneration and c2) of an enhancer of the glutathione-mediated conjugation.

It was found that the ability to detoxify is crucial for liver health in general. If the capacity of detoxification is reduced, the liver itself becomes toxified by all the endo- and exo-toxins it would normally neutralise.

As already pointed out above many drugs and toxins can be detoxified by conjugation with glutathione. If the detoxifying capacity via GSH of the body (liver) is exceeded other detoxification pathways will be used to a greater extent. The overall clearance will however be slower whereby body parts can be damaged which are exposed too heavily. Said parts can be for instance the liver, the respiratory tract, the gastrointestinal tract, and the skin. This could lead to respiratory diseases like COPD, emphyseme, CARA, and cancer, and liver diseases like fatty liver, cirrhosis, hepatitis and liver cancer.

In addition many people are exposed to toxic compounds that require an adequate glutathione metabolism. This applies for instance to people who live in polluted areas (radiation, numerous halogenated, nitrated chemicals), who work with dangerous chemicals (organophosphorus insecticides or halogenated solvents) and who smoke cigarettes. Also during chronic inflammation of tissue, which may occur in the case of arthritis or inflammatory bowel disease, the glutathione levels in the inflamed tissues are often depleted. Also in this case a further stimulation of the endogenous glutathione production will be advantageous.

The method and the compositions of the present invention can treat and/or prevent the above mentioned diseases. According to the invention the glutathione presence or the glutathione status, respectively, in the cells is increased or improved, respectively. This applies in particular for the treatment and/or prevention of impaired liver function.

The present invention is applicable for mammals including human beings and animals, for instance birds. Several diseases here described can occur during intensive animal breeding due to the consumption of an unbalanced feed diet. Liver problems occur due to the excessive amount of fats of inferior quality or the consumption of waste products of the human food industry which for some reason have become contaminated or comprise too high levels of anti-nutritional factors. This happens predominantly in pig and poultry breeding.

According to the present invention a glutathione precursor a) is administered in a certain minimum amount. Said precursor a) is either cysteine or one or more functional analogue(s) containing said amino acid cysteine or a combination of both. Said functional analogues are for instance salts and common esters of cysteine, especially of the L-isomer, N-alkylated derivatives of cysteine, such as N-acetyl cysteine (NAC), cysteine-rich proteins and peptides, such as some proteins from whey or egg, and cystathionine, both in reduced or oxidised form Glutathione itself in reduced or oxidised form can also increase glutathione tissue levels. When methionine or S-adenosylmethionine (SAM) are used as cystein analogues the risk for elevated cystein levels is high in animals including men suffering from impaired liver function. In case said compounds are used as cystein analogues at least folic acid, vitamin B6 and/or zinc should be present in addition. Preferably all three compounds are present in amounts that exceed the recommended daily amounts.

The Glutathione precursor used according to the invention can be a single species or a mixture of different components or species, respectively. The minimum amount of the precursor a) administered per day is at least 100 mg cysteine, calculated as free amino acid. The minimum amount is preferably at least 200 mg per day. The maximum amount of cysteine should not exceed 2000 mg. The absolute amounts of the equivalents can be easily calculated by using the molar weight of the above mentioned amino acid.

The precursor of glutathione a) is administered together with an enhancer of the glutathione biosynthesis b) and together with a third component c) described below. In a simple embodiment of the invention the above mentioned components a) b) and c) are administered or contained in the composition of the invention.

The third component c) administered is either one or more lignans or a combination of an enhancer of glutathione regeneration c1) and of an enhancer of the glutathione mediated conjugation c2). In this context it should be noted that lignans can act as an enhancer of glutathione regeneration c1) as well as an enhancer of the glutathione mediated conjugation c2). Consequently, according to a first embodiment of the present invention, the third component c) can consist of one lignan alone or a mixture of different lignans. According to a second embodiment of the invention the third component c) can be a combination of one or more lignans either with one enhancer or more enhancers of the glutathione biosynthesis c1) which is or are different from a lignan, or with one enhancer or more enhancers of the gutathione-mediated conjugation c2) which is or are different from a lignan. According to a third embodiment of the invention the third component c) can be a combination of one enhancer or more enhancers of the glutathione biosynthesis c1) which is or are different from a lignan with one enhancer ore more enhancers of the gutathione-mediated conjugation c2) which is or are also different from a lignan. According to a fourth embodiment of the invention the third component c) can be a combination of i) one enhancer or more enhancers of the glutathione biosynthesis c1) which is or are different from a lignan, ii) one enhancer or more enhancers of the gutathione-mediated conjugation c2) which is or are also different from and of iii) one lignan or more lignans.

According to a preferred embodiment the enhancer of the glutathione biosynthesis b) contains apocynin or analogues.

Apocynin can be isolated from plants such as Iris species (Iridaceae) or from the rhizome of *Apocynam cannabinum* or other Apocynaceae.

More preferably the enhancer of the glutathione biosynthesis b) is a preparation obtained from Picrorhiza species; even more preferably the enhancer of the glutathione biosynthesis b) is selected from the group consisting of an extract of *Picrorhiza kurrooa* and an extract of *Picrorhiza schrophulariiflora*, whereby said extract contains most preferably 0.01 to 100 mg per day apocynin or analogues.

The enhancer of glutathione regeneration c1) is preferably selected from the group consisting of preparations rich in silymarin, such as extracts from *Silybum marianum* or armurariu fruit, and preparations rich in schisandrins, such as extracts from Schisandra species; and the enhancer of glutathione-mediated detoxification process c2) is preferably selected from the group consisting of preparations rich in iridoid glycosides, especially extracts from Picrorhiza species, and preparations rich in Schisandrins such as extracts from Schisandra species.

The preparation of Picrorhiza species is preferably an extract from *Picrorhiza kurrooa* or *Picrorhiza scrophulariiflora* (also known as *Neopicrorhiza scrophulariiflora*), which contains preferably 1–100 mg of total iridoid glycosides, in particular 1 to 100 mg picrosides, more preferably 1 to 50 mg picroside II, for example about 6 mg picroside II, and 0.01–100 mg apocynin.

According to the invention, analogues of apocynin may be used instead of or in addition to apocynin. Such analogues are in particular those in which the 4-hydroxy group is etherified, especially with a sugar moiety. The analogue in which the sugar moiety is β-D-glucose is commonly known as androsin.

The preparation of *Silybum marianum* is preferably an extract containing 10–1000 mg silymarin, more preferably 175 mg of an extract containing 140 mg of silymarin.

The preparation of Schisandra species is preferably an extract from *Schisandra chienesis* or *Schisandra sphenanthera* containing 0.1–100 mg of lignans, in particular 0.1 to 100 mg schisandrins, more preferably 11 to 70 mg schisandrins, for example about 5 mg schisandrins.

The different components a), b), c), c1), and c2) are known and described above. Several traditionally used herbs, e.g. Milk thistle, Picrorhiza and Schisandra can be used, which are known to exhibit liver protective activities, and induce or enhance the endogenous glutathione production. This endogenous antioxidant plays a central role in the metabolisation and elimination of toxins. According to the present invention the GSH status in the liver is increased, and in addition, the enzyme γ-glutamylcysteine synthetase, responsible for GSH synthesis, is enhanced as well.

Therefore, the present invention includes precursors and cofactors important for glutathione synthesis, compounds that enhance glutathione regeneration, and compounds that induce the glutathione-mediated detoxification process.

Preferably, direct antioxidants like vitamin C, E, and flavonoids, and enzymatic antioxidants like selenium, zinc, copper, and manganese enhancing the antioxidant activity of the liver can be present in addition according to the present invention. This is preferred since several toxins are capable of exhibiting oxidative damage due to the formation of oxygen radicals.

Enzymatic antioxidants are in particular components that improve the activity of glutathione peroxidase or superoxide dismutase. Selenium can be used as selenium salt and preferably as selenium yeast that provides per daily dose 10–200 mcg selenium. Zinc can be present as an inorganic or organic zinc salt, such as ZnO providing preferably 0.1–30 mg zinc per daily dose. Copper can be present as a copper salt, providing preferably 0.1–8 mg copper per daily dose. Manganese can be present as a manganese salt, providing preferably 0.1–20 mg manganese per daily dose.

Furthermore, the composition can contain at least one compound that further enhances the glutathione status of the liver, as a cofactor in the biosynthesis of precursors of glutathione. Such a compound is selected from the group consisting of riboflavin, preferably 0.1–200 mg riboflavin, vitamin B6, preferably 0.1–200 mg vitamin B6, vitamin B12, preferably 0.1–3000 mcg vitamin B12, and folic acid or folate, preferably 10–1000 mcg folic acid. Preferred sources of vitamin B6 and vitamin B12 are pyridoxine and cyanocobalamine, respectively.

In addition, the composition can contain at least one component that enhances the antioxidant function by directly scavenging reactive oxygen species or by interfering with their formation. Such a component is selected from the group consisting of vitamin C, preferably 10–1000 mg vitamin C, vitamin E, preferably 1–800 mg α-TE, flavonoids, preferably an extract of *Matricaria recutita* containing 1–100 mg apigenin, catechins, preferably an extract of *Camellia sinensis* containing 1–500 mg catechins, and curcuminoids, preferably an extract of *Curcuma longa* containing 1–1000 mg curcumin.

As already pointed out above the present invention applies also to animals and in particular to pig and poultry breeding. In this case the components used according to the present invention can be present in the extracts of plants which are preferably used in animal feed. Said components can also be included in a premix for blending with regular animal feed. The premix is preferably based on whey proteins as source of the glutathione precursor a).

The compositions of the invention can have a form that is normally used for the administration of a food or of a food supplement. They can be present for instance as powders, liquids, emulsions, bars, tablets, and capsules which can be packaged in cartons, cans, sachets, bottles, bags (tea bags) and can be prepared according to methods known in the art.

A composition according to the invention in the form of a tablet contains for instance 300 mg glutathione, 20 mg apocynin and 5 mg schisandrins.

The invention is further described by the following, non limiting examples.

EXAMPLE 1

The following composition was mixed and prepared in a pill.

| Amount per serving (serving size 3 tablets) | | amount | unit |
| --- | --- | --- | --- |
| *Silybum marianum* (milk thistle) | fruit extract | 175 | mg |
| [providing silymarin (80%) | | 140 | mg] |
| *Camellia sinensis* (green tea) | leaf extract | 28.5 | mg |
| [providing catechins | | 20 | mg] |
| *Curcuma longa* (turmeric) | root extract | 10.5 | mg |
| [providing curcumin | | 10 | mg] |
| *Picrorhiza kurrooa* | rhizome extract | 120 | mg |
| [providing picrosides | | 6 | mg] |
| *Schisandra chinensis* | fruit extract | 55.6 | mg |
| [providing schisandrins | | 5 | mg] |
| *Matricaria recutita* (camomile) | flower extract | 625 | mg |
| [providing apigenin | | 15 | mg] |
| vitamin C (ascorbic acid) | | 54.2 | mg |
| [providing ascorbic acid | | 50 | mg] |
| vitamin E acetate succinate | | 6.8 10.9 | mg mg |
| [providing tocopherols | | 15.5 | [U] |
| Selenium yeast | | 14.7 | mg |
| [providing selenium | | 28 | mcg |
| Zinc oxide | | 3.8 | mg |
| [providing zinc | | 3 | mg |
| Cupric oxide | | 0.58 | mg |
| [providing copper | | 0.45 | mg] |
| Manganese gluconate dihydrate | | 7.2 | mg |
| [providing manganese | | 0.8 | mcg] |
| vitamin B12 | | 1.3 | mg |
| [providing cyanocobolamine | | 1.6 | mcg] |
| folic acid | | 0.27 | mg |
| [providing folate | | 200 | mcg] |
| N-acetylcysteine | | 202 | mg |
| [providing N-acetylcysteine | | 200 | mg] |

Other ingredients: Bulking agents: microcrystalline cellulose, calcium carbonate, croscarmellose sodium; Anti-caking agents: vegetable source stearic acid; vegetable stearate-glyceryl monostearate, silicon dioxide; Glazing agents: shellac, hydroxypropyl methyl cellulose, acetic acid esters of mono & diglycerides of fatty acids; Natural source colour: titanium dioxide; Thickeners: carnauba wax, xanthan gum; Emulsifiers: polysorbate 80.

Three tablets were administered daily, preferably combined with an additional multivitamin, to treat deprived liver function.

EXAMPLE 2

| Amount per daily dose | | amount | unit |
|---|---|---|---|
| *Silybum marianum* (milk thistle) | fruit extract | 175 | mg |
| *Curcuma longa* (turmeric) | root extract | 10.5 | mg |
| *Picrorhiza kurrooa* | rhizome extract | 360 | mg |
| *Schisandra chinensis* | fruit extract | 55.6 | mg |
| *Matricaria recutita* (camomile) | flower extract | 625 | mg |
| N-acetylcysteine | | 600 | mg |

EXAMPLE 3

| Amount per daily dose | amount | unit |
|---|---|---|
| *Silybum marianum* (milk thistle) | 175 | mg |
| *Picrorhiza kurrooa* | 360 | mg |
| N-acetylcysteine | 600 | mg |

Other ingredients known in the art of making a tablet

EXAMPLE 4

| Amount per daily dose | amount | unit |
|---|---|---|
| *Silybum marianum* (milk thistle) | 175 | mg |
| *Picrorhiza kurrooa* | 120 | mg |
| *Schisandra chinensis* | 55.6 | mg |
| Selenium yeast (about 0.2% selenium) | 15 | mg |
| Zinc oxide | 3.8 | mg |
| Copper oxide | 600 | mcg |
| Manganese gluconate | 7.2 | mg |
| N-acetylcysteine | 200 | mg |

Other ingredients known in the art of making a tablet

EXAMPLE 5

| Amount per daily dose | Amount | unit |
|---|---|---|
| *Silybum marianum* (milk thistle) | 175 | mg |
| *Picrorhiza kurrooa* | 120 | mg |
| vitamin B2 (riboflavin) | 1.25 | mg |
| vitamin B6 (pyridoxine) | 1.3 | mg |
| vitamin B12 premix (1% cyanocobalamin) | 0.18 | mg |
| folic acid (monoglutamate) | 200 | mcg |
| N-acetylcysteine | 1000 | mg |

Other ingredients known in the art of making a tablet

EXAMPLE 6

| Amount per daily dose | amount | unit |
|---|---|---|
| *Silybum marianum* (milk thistle) | 175 | mg |
| *Camellia sinensis* (green tea) | 28.5 | mg |
| *Curcuma longa* (turmeric) | 10.5 | mg |
| *Picrorhiza kurrooa* | 120 | mg |
| *Schisandra chinensis* | 55.6 | mg |
| *Matricaria recutita* (camomile) | 625 | mg |
| vitamin C (ascorbic acid) | 50 | mg |
| Alfa-tocopherol (vitamin E) | 10.4 | IU |
| N-acetylcysteine | 200 | mg |

Other ingredients known in the art of making a tablet

What is claimed is:

1. A method of increasing the presence of glutathione in cells including treating or reducing the risk of impaired liver function by administering to a mammal in the need thereof a composition which contains at least one of each of the following components:
   a) a precursor of glutathione which is selected from the group consisting of cysteine and functional equivalents of cysteine which yield cysteine when administered to said mammal, said cysteine being administered in an amount of at least 100 mg cysteine per day, wherein cysteine is calculated as free amino acid, or said functional equivalent of cysteine is administered in an amount which yields at least 100 mg of cysteine per day wherein cysteine is calculated as free amino acid;
   b) an enhancer of glutathione biosyntlesis containing apocynin or an analogue of apocynin which enhances glutathione biosynthesis; and
   c) a third component which is a combination
      c1) of an enhancer of glutathione regeneration and
      c2) of an enhancer of glutathione-mediated conjugation.

2. The method of increasing the presence of glutathione in cells according to claim 1 by administering a composition wherein
   the enhancer of the glutathione biosynthesis b) contains apocynin or an analogue of apocynin which enhances glutathione biosynthesis;
   the enhancer of glutathione regeneration c1) contains an active ingredient which is a lignan; and
   the enhancer of the glutathione-mediated conjugation c2) contains an active ingredient which is selected from the group consist of iridoid glycosides and lignans.

3. The method of claim 2 wherein said enhancer of glutathione regeneration contains an active ingredient which is silymarin.

4. The method of claim 2 wherein said analogue of apocynin which enhances glutathione biosynthesis is apocynin containing a 4-hydroxy group wherein said 4-hydroxy group is etherified.

5. The method of claim 4 wherein said 4-hydroxy group is etherified with a sugar moiety.

6. The method of claim 5 wherein said sugar moiety is β-D-glucose.

7. The method of claim 1 wherein said functional equivalents of cysteine are selected from the group consisting of salt of cysteine, ester of cysteine, N-alkylated derivative of cysteine, cysteine-rich protein, cysteine-rich peptide, glutathione in oxidized or reduced form, cystathionine, methionine and S-adenosylmethionine.

8. The method of claim 6 wherein said ester of cysteine is an ester of L-cysteine, said N-alkylated derivative of cysteine is N-acetyl cysteine, said cysteinerich protein is cysteine-rich protein from whey or egg, and said cystathinione is in reduced or oxidized form.

9. The method of increasing the presence of glutathione in cells according to claim 1 by administering a composition wherein
the enhancer of the glutathione biosynthesis b) is a preparation obtained from Picrorhiza species;
the enhancer of glutathione regeneration c1) is selected from the group consisting of a preparation of *Silybium marianum* and a preparation of Schisandra species; and
the enhancer of the glutathione-mediated conjugation c2) is selected from the group consisting of a preparation of Picrorhiza species and a preparation of Schisandra species.

10. The method of increasing the presence of glutathione in cells according to claim 1 wherein:
the precursor of glutathione a) comprises cysteine administered in an amount of 100 to 2000 mg per day;
the enhancer of the glutathione biosynthesis b) is selected from the group consisting of an extract of *Picrorhiza kurrooa* and an extract of *Picrorhiza schrophulariiflora*, wherein said extract contains apocynin or analogues thereof and is administered in an amount of 0.01 to 100 mg per day;
the enhancer of glutathione regeneration c1) is selected from the group consisting of an extract of *Silybum marianum* containing silymarin and an extract of *Schisandra chinensis* or *Schisandra phenanthera* containing schisandrins, said extract of *Silybum marianum* being administered in an amount of 10 to 1000 mg per day and said extract of *Schisandra chinesis* or *Schisandra phenanthera* being administered in an amount of 0.1 to 100 mg per day; and
the enhancer of the glutathione-mediated conjugation c2) is selected from the group consisting of an extract which contains picrosides obtained from *Picrorhiza kurrooa* or from *Picrorhiza schrophulariiflora* or from both Picrorhiza species, and of an extract which contains schisandrins obtained from *Schisandra chienesis* or from *Schisandra phenanthera* or from both Schisandra species; said extract which contains picrosides being administered in an amount of 1 to 100 mg per day and said extract containing schisandrins being administered in an amount of 0.1 to 100 mg per day.

11. The method of increasing the presence of glutathione in cells according to claim 1 wherein the composition further comprises an additional active ingredient d) which is selected from the group consisting of methionine and functional analogues containing said amino acid, folic acid, vitamin B12, vitamin B6, selenium yeast, a zinc salt, a copper salt, and a manganese salt.

12. The method of increasing the presence of glutathione in cells according to claim 11 wherein the active ingredient d) is selected from the group consisting of methionine administered in the amount of 100 to 1000 mg per day calculated as free amino acid, selenium yeast administered in an amount of 10 to 200 mcg per day, zinc oxide administered in an amount of 0.1 to 30 mg per day, cupric oxide administered in an amount of 0.1 to 8 mg per day, and manganese gluconate administered in an amount of 0.1 to 20 mg per day.

* * * * *